(12) United States Patent
Zhu et al.

(10) Patent No.: US 12,243,664 B2
(45) Date of Patent: Mar. 4, 2025

(54) TRIAZINE-BASED POLYMER

(71) Applicant: PolyJoule, Inc., Billerica, MA (US)

(72) Inventors: Zhengguo Zhu, Chelmsford, MA (US); Timothy Manning Swager, Newton, MA (US)

(73) Assignee: PolyJoule, Inc., Billerica, MA (US)

( * ) Notice: Subject to any disclaimer, the term of this patent is extended or adjusted under 35 U.S.C. 154(b) by 537 days.

(21) Appl. No.: 17/289,684

(22) PCT Filed: Oct. 28, 2019

(86) PCT No.: PCT/US2019/058308
§ 371 (c)(1),
(2) Date: Apr. 28, 2021

(87) PCT Pub. No.: WO2020/092214
PCT Pub. Date: May 7, 2020

(65) Prior Publication Data
US 2021/0403647 A1    Dec. 30, 2021

Related U.S. Application Data

(60) Provisional application No. 62/752,237, filed on Oct. 29, 2018.

(51) Int. Cl.
*H01B 1/12* (2006.01)
*C07D 251/18* (2006.01)
(Continued)

(52) U.S. Cl.
CPC .......... *H01B 1/128* (2013.01); *C07D 251/18* (2013.01); *C07D 251/28* (2013.01);
(Continued)

(58) Field of Classification Search
None
See application file for complete search history.

(56) References Cited

U.S. PATENT DOCUMENTS

2005/0196676 A1*  9/2005  Singh .................. H01M 8/1023
                                                          429/432
2013/0261274 A1   10/2013  Carlson et al.
(Continued)

FOREIGN PATENT DOCUMENTS

JP    2013229263 A   * 11/2013
WO    2015/192596 A1   12/2015

OTHER PUBLICATIONS

International Search Report and Written Opinion mailed Jan. 16, 2020, for Application No. PCT/US2019/058308.
(Continued)

*Primary Examiner* — Eric W Thomas
(74) *Attorney, Agent, or Firm* — Wolf, Greenfield & Sacks, P.C.

(57) ABSTRACT

Compositions and methods related to conducting polymeric compositions that can be used in devices for storage of electrical energy are generally provided. The composition may include redox active polymers that include an electrophilic nitrogen containing heterocycle and an electron rich aromatic compound. The electroactive polymers may be formed by polymerizing an electrophilic nitrogen containing heterocycle-based unit with an electron rich aromatic compound in the presence of heat and an acid-based catalyst. The resulting electroactive polymers may be suitable as polymer films for use as electrodes in energy storage devices. The polymer films disposed as electrodes can improve the energy density of such devices.

17 Claims, 4 Drawing Sheets

(51) Int. Cl.
*C07D 251/28* (2006.01)
*C08G 73/06* (2006.01)
*H01G 11/48* (2013.01)
*H01G 11/58* (2013.01)

(52) U.S. Cl.
CPC ......... *C08G 73/0644* (2013.01); *H01G 11/48* (2013.01); *H01G 11/58* (2013.01)

(56) References Cited

U.S. PATENT DOCUMENTS

2017/0218127 A1  8/2017  Dong et al.
2018/0174764 A1  6/2018  Hunter et al.

OTHER PUBLICATIONS

International Preliminary Report on Patentability mailed May 14, 2021, for Application No. PCT/US2019/058308.
Chen et al., Micro-/Mesoporous conjugated polymer based on star-shaped triazine-functional triphenylamine framework as the performance-improved cathode of Li-organic battery. J Polymer Science A Polymer Chem. Oct. 2018; 56(7850): 2574-83.

\* cited by examiner

TRIAZINE-BASED POLYMER

RELATED APPLICATIONS

This application is a national stage filing under 35 U.S.C. § 371 of international application number PCT/US2019/058308, filed Oct. 28, 2019, which claims priority under 35 U.S.C. § 119 (e) to U.S. provisional patent application, U.S. Ser. No. 62/752,237, filed Oct. 29, 2018, the entire contents of each which are incorporated herein by reference in its entirety.

FIELD OF THE INVENTION

The present invention generally relates to compositions such as triazine-based polymers and related devices.

BACKGROUND

The capacitance of traditional capacitors with metal electrode plates can generally range from about $10^{-12}$ farad (F) to about $10^{-3}$ F. Supercapacitors with capacitances of hundreds to thousands of farads, however, can result from employing large surface area carbon electrodes, as the capacitance is generally found to be proportional to the surface area of the electrodes. These devices allow up to between 18 kJ and 36 kJ of energy to be stored in 1 kg weight of the capacitor, referred to as the energy density. It would be desirable to further improve the energy density of such devices, and accordingly, improved compositions and methods are needed.

SUMMARY OF THE INVENTION

The present invention generally relates to compositions such as triazine-based polymers and related devices. The subject matter of the present invention involves, in some cases, interrelated products, alternative solutions to a particular problem, and/or a plurality of different uses of one or more systems and/or articles.

In some embodiments, a method for forming an electroactive polymer is described, wherein the method comprises providing a first monomer comprising an electrophilic nitrogen containing heterocycle substituted with halides, and/or a derivative thereof, providing a second monomer, wherein the second monomer comprises an electron rich aromatic compound, and polymerizing at least some of the first monomer and second monomer or mixtures of monomer to form a polymer, wherein polymerizing comprises heating the mixture to greater than or equal to 60° C. in the presence of an acid-based catalyst, and wherein the polymer comprises an electrophilic nitrogen containing heterocycle-based repeat unit.

In certain embodiments, a device is described, wherein the device comprises a current collector and an electrode comprising a polymer film in electrical communication with the current collector, the polymer film comprising a polymer formed by the polymerization of an electrophilic nitrogen containing heterocycle, and/or a derivative thereof, and an electron rich aromatic compound, wherein the device has an energy density of greater than or equal to 150 kJ/kg.

In some embodiments, a composition is described, wherein the composition comprises a polymer comprising a first monomeric unit comprising triazine and a second monomeric unit comprising an electron rich aromatic compound, at least a portion of the polymer comprising the first monomeric unit alternating with the second monomeric unit, wherein the electron rich aromatic compound is selected from the group consisting of triphenylamine, 1,3,5-triphenylbenzene, dibenzothiophene, nathphalene, N-phenyl-carbazole, and derivatives thereof, any of which is optionally substituted, and/or combinations thereof.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Compositions and methods related to conducting polymeric compositions that can be used for the storage of electrical energy are generally provided. In some embodiments, the composition comprises redox active polymers comprising an electrophilic nitrogen containing heterocycle and an electron rich aromatic compound. In some embodiments, the composition comprises a triazine-based polymer. The electroactive polymers may be formed, in some cases, by polymerizing an electrophilic nitrogen containing heterocycle-based unit with an electron rich aromatic compound in the presence of heat and an acid-based catalyst. The resulting electroactive polymers may be suitable as polymer films for use as electrodes in energy storage devices. The polymer films disposed as electrodes can improve the energy density of such devices.

Conducting polymers have a relatively high charge density and a low cost of manufacturing when compared to expensive electrode materials, such as metal oxides (e.g., $RuO_2$, $IrO_2$, and $PtO_2$). Polymeric compounds such as polyanilines, polypyrroles, and polythiophenes, for example, have been evaluated as conducting materials for electrode applications in capacitors. When disposed as electrodes, such conducting polymers can cause capacitors to reach specific capacitances as high as 600 F/g. In almost all cases, however, the maximum operating voltage in capacitors with conducting polymers is small (around 1 V), due to issues with stability.

Figure 1:
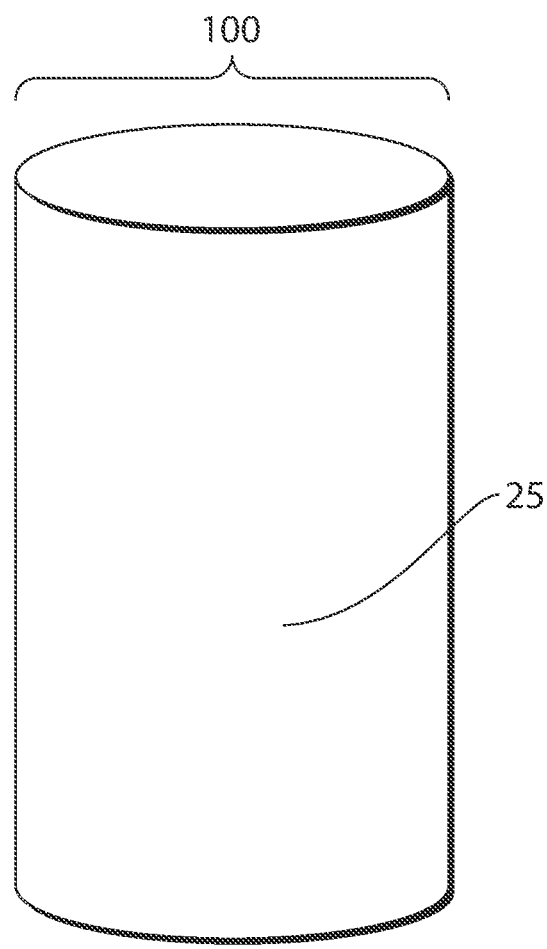
FIG. 1 shows a schematic representation of an exemplary polymer film disposed as an electrode, according to certain embodiments.

The Inventors have discovered that redox active polymers containing co-repeating units of an electrophilic nitrogen containing heterocycle and an electron rich aromatic compound can be used as continuous substrate films for use as electrodes in energy storage devices (e.g., capacitors). FIG. 1, for example, shows a schematic representation of an exemplary polymer film disposed as an electrode. As shown in FIG. 1, polymer film 25 is disposed as electrode 100. Advantageously, the redox active polymers described herein may have improved electrochemical properties over traditional conducting polymers. In some embodiments, employing conducting polymer films as electrodes can improve the energy density of capacitors by deriving further capacitance from the storage of charge in the bulk of the material in response to the voltage change between electrodes. In some embodiments, adjusting one or more co-repeating monomeric units and/or the ratio between the co-repeating monomeric units in the conducting polymer film can provide superior negative and/or positive electrodes for capacitors with higher energy densities.

According to certain embodiments, the compositions described herein comprise a polymer (e.g., an electroactive polymer). In some embodiments, the polymer comprises a first monomeric unit and a second monomeric unit. In certain embodiments, the electroactive polymer may be a film. In certain embodiments, at least a portion of the polymer comprises the first monomeric unit alternating with the second monomeric unit. According to some embodiments, the first monomeric unit and second monomeric unit may alternate, for example, in any of a variety of suitable ways that are described in greater detail below.

In some embodiments, the first monomeric unit may be an electrophilic nitrogen containing heterocycle-based unit, or a derivative thereof. According to certain embodiments, the polymer may comprise an electrophilic nitrogen containing heterocycle-based repeat unit.

According to some embodiments, the electrophilic nitrogen containing heterocycle is based on triazine or a triazine-derivative (e.g., a substituted triazine, a functionalized triazine, and the like). In certain embodiments, the electrophilic nitrogen containing heterocycle is substituted with halides. In some embodiments, the electrophilic nitrogen containing heterocycle is cyanuric chloride. In certain embodiments, the electrophilic nitrogen containing heterocycle comprises 2,1,3-benzothiadiazole (e.g., 2,1,3-benzothiadiazole-triphenylamine).

In some embodiments, the second monomeric unit comprises an electron rich aromatic compound. According to certain embodiments, the electron rich aromatic compound may be an electron rich polyaromatic compound. In certain embodiments, the electron rich aromatic compound comprises two or more phenyl groups. For example, in certain embodiments, the electron rich aromatic compound may be 1,3,5-triphenylbenzene, dibenzothiophene, triphenylamine, nathphalene, N-phenyl-carbazole, and/or derivatives thereof, any of which is optionally substituted with, for example, toluene, benzene, and/or thiophene, and/or combinations thereof.

Certain embodiments described herein are related to a method of forming an electroactive polymer. In some embodiments, the method may comprise providing a first monomer comprising an electrophilic nitrogen containing heterocycle, and/or a derivative thereof. In some embodiments, the electrophilic nitrogen containing heterocycle may be substituted with halides. The method may further comprise providing a second monomer comprising an electron rich aromatic compound.

Figure 2:
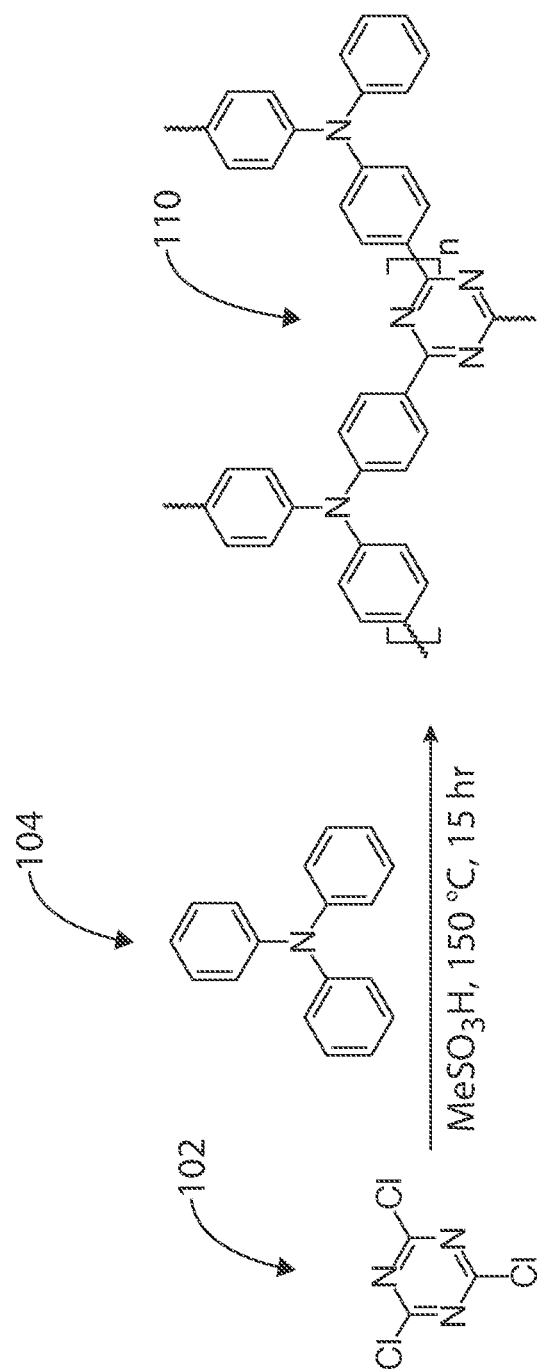
FIG. 2 shows a polymerization reaction between cyanuric chloride and triphenylamine, according to some embodiments.

According to certain embodiments, the method of forming an electroactive polymer comprises polymerizing at least some of the first monomer and second monomer or mixtures of monomer to form a polymer. FIG. 2 shows, according to certain non-limiting embodiments, a polymerization reaction between a first monomer (e.g., cyanuric chloride) and a second monomer (e.g., triphenylamine). As shown in FIG. 2, first monomer 102, an electrophilic nitrogen containing heterocycle, and second monomer 104, an electron rich aromatic compound, can polymerize to provide polymer 110. According to certain embodiments, the polymerizing can occur due to the electronic attraction between the electrophilic nitrogen containing heterocycle and the electron rich aromatic compound.

In some embodiments, the polymerizing comprises heating the mixture (e.g., the first monomer and the second monomer) to greater than or equal to 60° C. For example, according to certain embodiments, the polymerizing comprises heating the mixture to greater than or equal to 60° C., greater than or equal to 75° C., greater than or equal to 100° C., greater than or equal to 125° C., greater than or equal to 150° C., greater than or equal to 175° C., greater than or equal to 200° C., greater than or equal to 225° C., or greater than or equal to 250° C. According to certain embodiments, the polymerizing comprises heating the mixture to less than or equal to 300° C., less than or equal to 250° C., less than or equal to 225° C., less than or equal to 200° C., less than or equal to 175° C., less than or equal to 150° C., less than or equal to 125° C., less than or equal to 100° C., or less than or equal to 75° C. Combinations of the above recited ranges are also possible (e.g., the polymerizing comprises heating the mixture to greater than or equal to 60° C. and less than or equal to 300° C., the polymerizing comprises heating the mixture to greater than or equal to 125° C. and less than or equal to 200° C.).

In certain embodiments, the polymerizing is done in the presence of an acid-based catalyst. According to certain embodiments, the acid-based catalyst is a Brønsted acid. For example, in certain embodiments, the acid-based catalyst is p-toluenesulfonic acid, $H_3PO_4$, $CH_3SO_3H$, and the like. In some embodiments, the acid-based catalyst is a Lewis acid. For example, in certain embodiments, the acid-based catalyst comprises $AlCl_3$, $BF_3$ and the like.

According to certain embodiments, the molar ratio of the first monomeric unit to the second monomeric unit in the polymer may be any of a variety of suitable amounts. For example, according to certain embodiments, the molar ratio of the first monomeric unit to the second monomeric unit in the polymer may be greater than or equal to 1:1. In certain embodiments, the molar ratio of the first monomeric unit to the second monomeric unit in the polymer may be greater than or equal to 1:2, greater than or equal to 1:3, greater than or equal to 1:4, greater than or equal to 1:5, greater than or equal to 1:10, greater than or equal to 1:20, greater than or equal to 1:30, greater than or equal to 1:50, greater than or equal to 1:75, or greater than or equal to 1:90. In some embodiments, the molar ratio of the first monomeric unit to the second monomeric unit in the polymer may less than or equal to 1:100, less than or equal to 1:90, less than or equal to 1:75, less than or equal to 1:50, less than or equal to 1:30, less than or equal to 1:20, less than or equal to 1:10, less than or equal to 1:5, less than or equal to 1:4, less than or equal to 1:3, or less than or equal to 1:2. Combinations of the above recited ranges are also possible (e.g., the molar ratio of the first monomeric unit to the second monomeric unit in the polymer may be greater than or equal to 1:1 and less than or equal to 1:100, the molar ratio of the first monomeric unit to the second monomeric unit may be greater than or equal to 1:5 and less than or equal to 1:50).

In some embodiments, the molar ratio of the first monomeric unit to the second monomeric unit in the polymer may be greater than or equal to 2:1, greater than or equal to 3:1, greater than or equal to 4:1, greater than or equal to 5:1, greater than or equal to 10:1, greater than or equal to 20:1, greater than or equal to 30:1, greater than or equal to 50:1, greater than or equal to 75:1, or greater than or equal to 90:1. According to some embodiments, the molar ratio of the first monomeric unit to the second monomeric unit in the polymer may be less than or equal to 100:1, less than or equal to 75:1, less than or equal to 50:1, less than or equal to 30:1, less than or equal to 20:1, less than or equal to 10:1, less than or equal to 5:1, less than or equal to 3:1, or less than or equal to 2:1. Combinations of the above recited ranges are also possible (e.g., the molar ratio of the first monomeric unit to the second monomeric unit in the polymer may be greater than or equal to 2:1 and less than or equal to 100:1, the molar ratio of the first monomeric unit to the second monomeric unit in the polymer may be greater than or equal to 5:1 and less than or equal to 50:1).

According to certain embodiments, following the synthesis of the electroactive polymer, the electroactive polymer may be post-processed into a film for use as an electrode in an energy storage device (e.g., a capacitor). In some embodiments, the polymer may comprise a polymer formed by the polymerization of an electrophilic nitrogen containing heterocycle and/or a derivative thereof, and an electron rich aromatic compound. The polymer may be rolled, kneaded, and/or pressed into a polymer film, according to certain embodiments. In certain embodiments, the polymer may be added to a fluid (e.g., a liquid solvent), thereby forming a slurry, which may be coated onto one or more current collectors. In some cases, the polymer film may comprise highly crystalline polymers (e.g. solid state structures). According to some embodiments, the polymer film may comprise amorphous polymers.

In some embodiments, energy storage devices are described. According to certain embodiments, a device may comprise a current collector and an electrode comprising a polymer film comprising a polymer formed by the polymerization of an electrophilic nitrogen containing heterocycle and/or a derivative thereof, and an electron rich aromatic compound. In certain embodiments, the polymer film may be disposed as an electrode in the energy storage device (e.g., a capacitor) in electrochemical communication with the current collector. For example, in some embodiments, polymer layer 25 is disposed electrode 100, as shown in FIG. 1. Electrode 100, in some embodiments, may be in electrochemical communication with a current collector.

The energy storage device may be an electrochemical double-layer capacitor, also known as a supercapacitor, supercondenser, or ultracapacitor. Typically, the device may store energy (e.g., electric energy) in an electric field that is established by charge separation at an interface between two electroactive materials (e.g., electrode and electrolyte). A general embodiment of an energy storage device can include a first electrode, a second electrode in electrochemical communication with the first electrode, and a separator material arranged between the first and second electrodes. In some embodiments, the first electrode is a cathode and the second electrode is an anode. In some embodiments, the first electrode is an anode and the second electrode is a cathode. According to certain embodiments, the second electrode is substantially separated from the first electrode. In some embodiments, the second electrode and/or first electrode may comprise a conductive carbon material. The device includes an electrolyte or other mobile phase that can dissociate into anions and cations in contact with both electrodes. The components of the device may be assembled such that the electrolyte is arranged between the first and second electrodes. In some embodiments, the components of the device may be assembled such that the electrolyte is distributed throughout the bulk of the electrodes and the separator material.

Figure 3:
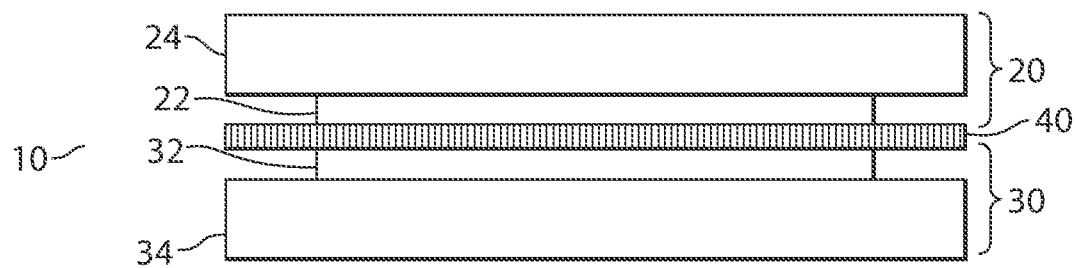
FIG. 3 shows a schematic representation of an energy storage device, according to certain embodiments.

FIG. 3 shows an illustrative embodiment of a device as described herein. In the embodiment shown, device 10 (e.g., energy storage device) includes a first electrode 20, which comprises first conductive material 22 (e.g., first electrically conductive material) in contact with a substrate 24. In certain embodiments, first conductive material 22 and substrate 24 may be the same composition (e.g., electroactive polymers). Second electrode 30, in some embodiments, comprises second conductive material 32 in contact with substrate 34. Second conductive material 32 (e.g., second electrically conductive material) and substrate 34 may be the same composition (e.g., electroactive polymers). According to some embodiments, first electrode 20 and second electrode 30 may be arranged in the device such that thy are in electrochemical communication with each other (e.g., via a separator material). Separator material 40 can be placed adjacent to first electrode 20 and second electrode 30. Conductive material 32 may be in contact with a surface of separator material 40 that is opposed to the surface of separator material 40 that is in contact with first conductive material 22. An electrolyte may be arranged between first electrode 20 and second electrode 30 (e.g., via separator material 40), such that the electrolyte is in contact with first electrode 20 and second electrode 30. It should be understood that there are other embodiments in which the orientation of the components is varied. In some embodiments, one or more of the device components can be formed as thin films. For example, according to certain embodiments, first electrode 20 comprising substrate 24 and first conductive material 22 may be a thin film and/or second electrode 30 comprising substrate 34 and second conductive material 32 may be a thin film.

In some embodiments, a device may be charged and/or discharged during normal operation. According to certain embodiments, the energy storage device may have to be charged and/or discharged in order to store energy (e.g., as energy density of the device). Therefore, in certain embodiments, the device can be charged and/or discharged at a potential window between 0 V and 3.5 V. According to some embodiments, the potential window of the device may change depending on the composition of components in the energy storage device (e.g., electrolyte). In certain embodiments, the potential window of the device may change depending on the composition and/or arrangement the one or more electrodes (e.g., the cathode and/or anode). For example, in a non-limiting embodiment, the potential window of the device may change depending on the polymer film disposed as one or more electrodes.

According to some embodiments, the electrically conductive polymers described herein may have substantially the same and/or improved electrochemical properties (e.g., conductivity) as a theoretical polymer of the electrophilic nitrogen containing heterocycle or a theoretical polymer of the electron rich aromatic compound. A film of the electrically conductive polymers may be disposed into a device (e.g., a capacitor) as an electrode (e.g., in electrical communication with a current collector), such that the polymer has any of a variety suitable energy densities. According to certain embodiments, the electrically conductive polymer film has an energy density of greater than or equal to 50 kJ/kg. In some aspects, for example, the electrically conductive polymer film may have an energy density of between 50 kJ/kg and 2000 kJ/kg. In certain embodiments, the electrically conductive polymer film may have an energy density of greater than or equal to 50 kJ/kg, greater than or equal to 100 kJ/kg, greater than or equal to 200 kJ/kg, greater than or equal to 300 kJ/kg, greater than or equal to 400 kJ/kg, greater than or equal to 500 kJ/kg, greater than or equal to 600 kJ/kg, greater than or equal to 700 kJ/kg, greater than or equal to 800 kJ/kg, greater than or equal to 900 kJ/kg, greater than or equal to 1000 kJ/kg, greater than or equal to 1100 kJ/kg, greater than or equal to 1200 kJ/kg, greater than or equal to 1300 kJ/kg, greater than or equal to 1400 kJ/kg, greater than or equal to 1500 kJ/kg, greater than or equal to 1600 kJ/kg, greater than or equal to 1700 kJ/kg, greater than or equal to 1800 kJ/kg, or greater than or equal to 1900 kJ/kg. In some embodiments, the electrically conductive polymer film may have an energy density of less than or equal to 2000 kJ/kg, less than or equal to 1900 kJ/kg, less than or equal to 1800 kJ/kg, less than or equal to 1700 kJ/kg, less than or equal to 1600 kJ/kg, less than or equal to 1500 kJ/kg, less than or equal to 1400 kJ/kg, less than or equal to 1300 kJ/kg, less than or equal to 1200 kJ/kg, less than or equal to 1000 kJ/mol, less than or equal to 900 kJ/kg, less than or equal to 800 kJ/kg, less than or equal to 700 kJ/kg, less than or equal to 600 kJ/kg, less than or equal to 500 kJ/kg, less than or equal to 400 kJ/kg, less than or equal to 300 kJ/kg, less than or equal to 200 kJ/kg, or less than or equal to 100 kJ/mol. Combinations of the above recited ranges are also possible (e.g., the device comprising the electrically conductive polymer has an energy density greater than or equal to 50 kJ/kg and less than or equal to 1000 kJ/kg, the device comprising the electrically conductive polymer film has an energy density greater than or equal to 500 kJ/kg and less than or equal to 2000 kJ/kg). According to some embodiments, the energy density of the device comprising the electrically conductive polymer film may be the gravimetric energy density of the device. The energy density of the device comprising the electrically conductive polymer film may be calculated, in some embodiments, based on the total energy stored divided by the total mass of the polymer film.

According to certain embodiments, a device may comprise a first electrode and a second electrode separated from the first electrode (e.g., by one or more layers). In some embodiments, the first electrode and/or the second electrode may comprise a conductive carbon material. For example, in certain embodiments, the first electrode and/or second electrode may comprise activated carbon and/or Ketjenblack. Electrodes described herein may include additional components that may improve the performance, stability and/or other properties of the electrode. For example, the electrode may include an additive conductive material (e.g., a conductive powder), and may further include a material that binds the powder particles together. Examples of other additives or modifiers include metal salts, metal oxides, polydimethylsiloxane, polystyrene, polypropylene, silicone oil, mineral oil, paraffin, a cellulosic polymer, polybutadiene, polyneopropene, polytetrafluoroethylene, natural rubber, polyimide, or other polymers.

The device may further include an electrolyte arranged to be in electrochemical communication with the first and second electrodes (e.g., the first electrode and second electrode are in contact with a common electrolyte). The electrolyte can be any of a variety of materials capable of transporting either positively or negatively charged ions or both between two electrodes and should be chemically compatible with the electrodes.

In some cases, the electrolyte is selected to be capable of supporting high charge stabilization.

In some embodiments the electrolyte is a liquid electrolyte. In one set of embodiments, the electrolyte is an ionic liquid. Other examples of electrolytes include ethylene carbonate solutions or propylene carbonate solutions, either of which include at least one salt having the formula, $[(R)_4N^+][X^-]$, wherein X is $(PF_6)^-$, $(BF_4)^-$, $(SO_3R^a)^-$, $(R^aSO_2-N-SO_2R^a)^-$, or $((CF_3)_2CHO)^-$, wherein R is alkyl and $R^a$ is alkyl, aryl, fluorinated alkyl, or fluorinated aryl. In certain embodiments, the liquid electrolyte comprises N-ethyl-N-(2-methoxyethyl)-N,N-dimethylammonium tetrafluoroborate and/or 1-ethyl-3-methylimidazolium tetrafluoroborate. According to some embodiments, the liquid electrolyte comprises dimethyl carbonate, ethyl methyl carbonate, diethyl carbonate, ethylene carbonate, propylene carbonate, and/or acetonitrile.

According to certain embodiments, the electrolyte may comprise a separator. The separator material may be any material capable of physically separating the first and second electrodes, while also allowing fluids and/or charged species (e.g., electrolyte) to travel from one electrode to another. The separator material may also be selected to be chemically inert to other components of the device, so as to not interfere with device performance (e.g., charge/discharge of the device). In some cases, the separator material is or comprises paper. In some cases, the separator material is or comprises a polymer. For example, the polymer may include polypropylene, polyethylene, cellulose, a polyarylether, or a fluoropolymer.

In one embodiment, the first and second electrodes may be placed on opposite surfaces of a substantially planar separator material wherein the thickness of the separator material determines the distance between the electrodes.

As used herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl has 12 or fewer carbon atoms in its backbone (e.g., C1-C12 for straight chain, C3-C12 for branched chain), or, in some cases, 6 or fewer, or 4 or fewer. Likewise, some cycloalkyls have from 3-10 carbon atoms in their ring structure, or have 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The term "heteroaryl" refers to aryl groups comprising at least one heteroatom as a ring atom.

The term "heterocyclyl" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures, or in some cases 3- to 7-membered rings, whose ring structures include one to four heteroatoms. The term "heterocycle" may include heteroaryl groups (e.g., aromatic heterocycles), saturated heterocycles (e.g., cycloheteroalkyl) groups, or combinations thereof. The heterocycle may be a saturated molecule, or may comprise one or more double bonds. In some case, the heterocycle is an aromatic heterocycle, such as pyrrole, pyridine, and the like. In some cases, the heterocycle may be attached to, or fused to, additional rings to form a polycyclic group. In some cases, the heterocycle may be part of a macrocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

As used herein, the term "halo" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl or aryl, the above formula represents a "ketone" group (e.g., alkylcarbonyl, arylcarbonyl, etc.). Where W is hydrogen, the above formula represents an "aldehyde" group.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, aralkyloxyalkyl, and the like.

EXAMPLES AND EMBODIMENTS

Example 1

The following example describes the synthesis of poly (triphenylamine-co-triazine). Cyanuric chloride and triphenylamine were placed in a flask. Methanesulfonic acid was added to the reaction mixture. The reaction mixture was heated to 150° C. for 20 hours, then cooled to room temperature, and 150-250 mL of water was added. The solids were collected by filtration, washed first with water, then an aqueous solution of sodium hydroxide (10%), then water, and finally methanol. The gray solids were dried in vacuo at 70° C. for 24 hours, providing a yield of 95-100%.

Example 2

The following example describes the preparation of activated carbon films. Activated carbon was mixed with polytetrafluoroethylene (PTFE) and water. The resulting mixture was kneaded into dough and rolled into a film using a rolling mill. The film was then cut into desirable shapes and sizes to be used as electrodes in supercapacitor devices.

Example 3

The following example describes the preparation of a triazine-containing polymer film. Cyanuric chloride was mixed with Ketjenblack, PTFE, and water. The resulting dough was rolled into a film on a rolling mill. The film was then dried under vacuum and cut into desirable shapes and sizes to be used as positive electrodes in supercapacitor devices.

Example 4

Figure 4:
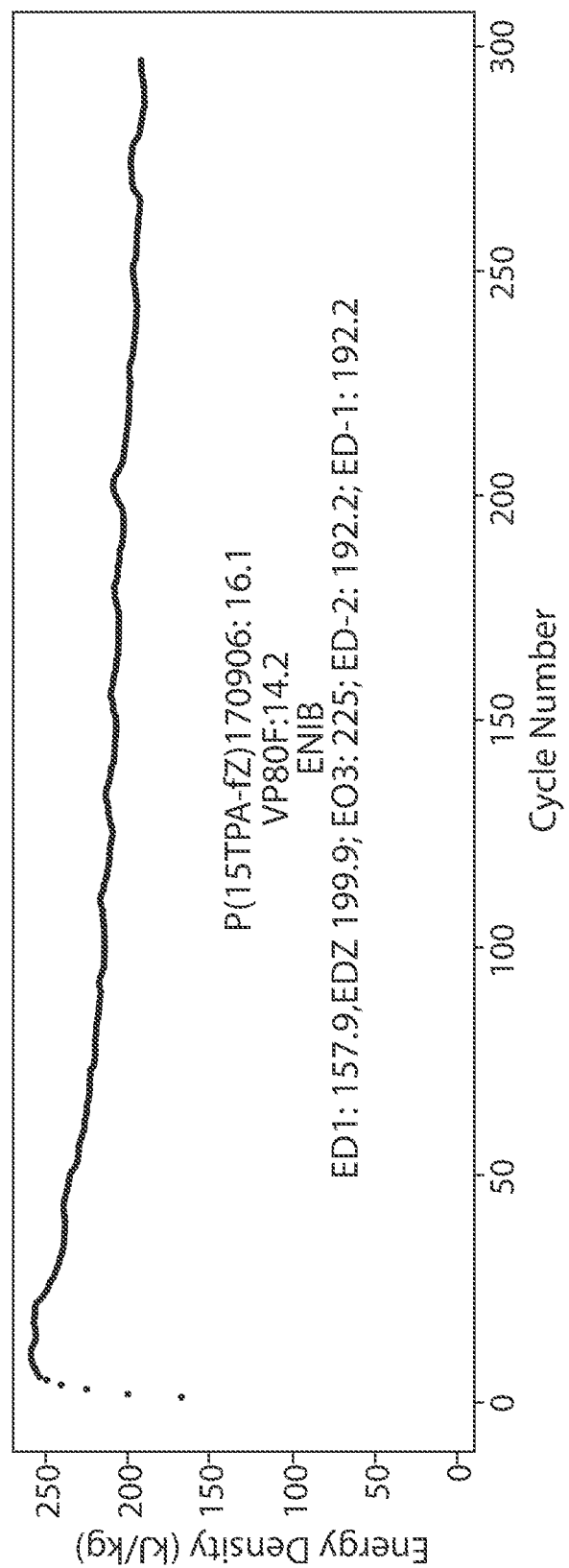
FIG. 4 shows the energy density profile of a single cell capacitor over 300 cycles, according to some embodiments.

The following example describes the preparation of single cell capacitors using a blend of poly(triphenylamine-co-triazine), Ketjenblack, and PTFE as a positive electrode. In a non-limiting procedure, a film made of a blend of poly(triphenylamine-co-triazine), Ketjenblack, PTFE, an activated carbon film, and a cellulose separator, all saturated with an ionic liquid electrolyte, were assembled with glassy carbon as a current collector. The completed assembly was compressed together. The device was tested by passing a constant current into the triazine polymer film from the activated carbon film, until the potential difference between the two electrodes reached 3.5 V, and then the direction of the current was reversed. The energy density of the device was calculated by dividing the energy released during each cycle by the total weight of the electrode materials. The representative energy density of the device tested over 300 cycles is shown in FIG. 4.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A device, comprising:
    a current collector; and
    an electrode comprising a polymer film in electrical communication with the current collector, the polymer film comprising a polymer formed by polymerization of an electrophilic nitrogen containing heterocycle, substituted or unsubstituted, and/or a derivative thereof, and an electron rich aromatic compound,
    wherein the device has an energy density of greater than or equal to 150 kJ/kg.

2. The device of claim 1, wherein the electrophilic nitrogen containing heterocycle is substituted with halides.

3. The device of claim 2, wherein the device has an energy density of greater than or equal to 180 KJ/kg.

4. The device of claim 2, wherein the electrophilic nitrogen containing heterocycle is cyanuric chloride.

5. The device of claim 1, wherein the electrode is a first electrode.

6. The device of claim 5, further comprising a second electrode substantially separated from the first electrode.

7. The device of claim 6, wherein the first electrode and the second electrode are in contact with a common electrolyte.

8. The device of claim 7, wherein the electrolyte is a liquid electrolyte.

9. The device of claim 8, wherein the liquid electrolyte comprises N-ethyl-N -(2-methoxyethyl)-N,N-dimethylammonium tetrafluoroborate, 1-ethyl-3-methylimidazolium tetrafluoroborate, dimethyl carbonate, ethyl methyl carbonate, diethyl carbonate, ethylene carbonate, propylene carbonate, and/or acetonitrile.

10. The device of claim 6, further comprising a separator arranged between the first electrode and the second electrode.

11. The device of claim 6, wherein the first electrode and/or the second electrode comprises a conductive carbon material.

12. The device of claim 1, wherein the electrophilic nitrogen containing heterocycle comprises 2,1,3-benzothiadiazole.

13. The device of claim 12, wherein the electrophilic nitrogen containing heterocycle is substituted with halides.

14. The device of claim 1, wherein the polymer film comprises an electrophilic nitrogen containing heterocycle-based repeat unit.

15. The device of claim 14, wherein the electrophilic nitrogen containing heterocycle-based repeat unit is based on triazine or a derivative thereof.

16. The device of claim 1, wherein the electron rich aromatic compound is selected from the group consisting of triphenylamine, 1,3,5-triphenylbenzene, dibenzothiophene, naphthalene, N-phenyl-carbazole, and derivatives thereof, any of which is optionally substituted, and/or combinations thereof.

17. The device of claim 1, wherein the electron rich aromatic compound comprises two or more phenyl groups.

* * * * *

UNITED STATES PATENT AND TRADEMARK OFFICE
CERTIFICATE OF CORRECTION

PATENT NO. : 12,243,664 B2
APPLICATION NO. : 17/289684
DATED : March 4, 2025
INVENTOR(S) : Zhengguo Zhu et al.

Page 1 of 1

It is certified that error appears in the above-identified patent and that said Letters Patent is hereby corrected as shown below:

In the Claims

At Column 13, Line 21, Claim 3, the "K" should be "k".

Signed and Sealed this
Fifteenth Day of April, 2025

Coke Morgan Stewart
*Acting Director of the United States Patent and Trademark Office*